US010870016B2

(12) United States Patent
Hamilton et al.

(10) Patent No.: US 10,870,016 B2
(45) Date of Patent: *Dec. 22, 2020

(54) LASER IONIZATION THERAPY ASSEMBLY

(71) Applicant: IN CYNC SPORTS CLINIC, Littleton, CO (US)

(72) Inventors: Scott Hamilton, Littleton, CO (US); James Steve Hamilton, Littleton, CO (US)

(73) Assignee: IN CYNC SPORTS CLINIC, Littleton, CO (US)

( * ) Notice: Subject to any disclaimer, the term of this patent is extended or adjusted under 35 U.S.C. 154(b) by 175 days.

This patent is subject to a terminal disclaimer.

(21) Appl. No.: 16/129,625

(22) Filed: Sep. 12, 2018

(65) Prior Publication Data
US 2019/0143139 A1 May 16, 2019

Related U.S. Application Data

(63) Continuation of application No. 14/923,533, filed on Oct. 27, 2015, now Pat. No. 10,099,066.

(51) Int. Cl.
*A61N 5/06* (2006.01)
*A61N 1/44* (2006.01)
*A61N 5/067* (2006.01)

(52) U.S. Cl.
CPC .......... *A61N 5/0619* (2013.01); *A61N 1/445* (2013.01); *A61N 2005/067* (2013.01); *A61N 2005/0651* (2013.01); *A61N 2005/0663* (2013.01); *A61N 2005/0668* (2013.01)

(58) Field of Classification Search
CPC .................. A61N 5/0619; A61N 1/445; A61N 2005/0651; A61N 2005/0663; A61N 2005/0668; A61N 2005/067

USPC .......................................................... 607/80
See application file for complete search history.

(56) References Cited

U.S. PATENT DOCUMENTS

| | | | |
|---|---|---|---|
| 4,438,498 | A | 3/1984 | Sekel et al. |
| 4,696,721 | A | 9/1987 | Higashino et al. |
| 5,514,168 | A | 5/1996 | Friedman |
| 6,280,591 | B1 | 8/2001 | Akutsu et al. |
| 6,929,934 | B1 | 8/2005 | Korchev et al. |
| 10,099,066 | B2 * | 10/2018 | Hamilton ............. A61N 5/0619 |

(Continued)

OTHER PUBLICATIONS

"Ionization Therapy: Modern Technology Applied to an Ancient Problem" originally published in Explore! For the Professional, vol. 11, No. 4, 2002, staff writer.

*Primary Examiner* — Aaron F Roane
(74) *Attorney, Agent, or Firm* — Dentons US LLP

(57) ABSTRACT

A laser ionization therapy assembly having a reservoir defined by a peripheral wall and a base; a support device having a support coupling member and a support opening; and a laser module accommodating a laser diode, the laser module having an opening and a laser module coupling member, wherein the support device is fixedly attached to the peripheral wall of the reservoir and the laser module is detachably coupled thereto, wherein the laser diode is positioned at an angle relative to the base of the reservoir so that laser light is directed through the openings of the laser module and support device to a predetermined location within the reservoir at a height of between ½ inch to 1 inch above the base, and wherein the laser light has a wavelength of between about 630 and 640 nm and a peak power of about 10 mW.

15 Claims, 23 Drawing Sheets

(56) References Cited

U.S. PATENT DOCUMENTS

2003/0034249 A1    2/2003   Akutsu et al.
2003/0136205 A1    7/2003   Totoki
2008/0114418 A1    5/2008   Myeong et al.

* cited by examiner

600

3000

LASER IONIZATION THERAPY ASSEMBLY

This application is a Continuation of U.S. patent application Ser. No. 14/923,533, filed on Oct. 27, 2015, now allowed, which is hereby incorporated by reference in its entirety for all purposes as if fully set forth herein.

BACKGROUND OF THE INVENTION

Field of the Invention

The present invention relates to a laser ionization therapy assembly. More particularly, the assembly supports a laser module that is used to conduct laser ionization therapy. The assembly includes a support mechanism that is coupled to the laser module and attached to a reservoir, such that the laser module is hands free during a laser ionization therapy session. The support mechanism is configured such that laser light emitted from the laser module is directed to a predetermined location within the reservoir.

Discussion of the Related Art

The benefits of using cold laser therapy in the area of chiropractic, osteopathic, naturopathic, and acupuncture therapy in reducing pain and swelling, promoting healing processes, treating old injuries, etc., are well-known. Cold laser therapy uses a low intensity beam of laser light that is capable of stimulating natural healing processes at a cellular level. This has proven effective in the area of chiropractic therapy in reducing pain and swelling, promoting healing processes, in treating old injuries, etc.

U.S. Pat. Nos. 6,913,616 and 7,458,983, which are incorporated by reference herein, discuss electronic systems for laser ionization therapy for detoxification. The systems discussed in those patents use a cold laser unit that requires either a handheld laser probe for directing laser light to a particular area of a user's body, or physically arranging the cold laser unit so that it is positioned to direct laser light to a particular area of the user's body. In the case of the handheld laser probe configuration, an operator other than the user being treated is required to hold the laser probe. In the case of physically positioning the cold laser unit so that the laser light will be directed to a particular area of the user's body, this procedure is time consuming and inexact, and often takes several trials and errors before the cold laser unit is properly positioned.

Accordingly, it is an object of the invention to provide a laser ionization therapy assembly and method capable of improving a user's health, such as by efficiently removing toxins from a user's body, whereby a laser module is attached to a reservoir at a predetermined location of the reservoir and configured to emit light though the reservoir to irradiate a predetermined area of the user's body.

SUMMARY OF THE INVENTION

The invention is directed to a laser ionization therapy system and method that substantially obviates one or more problems due to limitations and disadvantages of the related art.

To achieve these advantages, the laser ionization therapy system may include a laser module attached to a reservoir at a predetermined location of the reservoir, wherein the laser module includes laser diodes positioned therein such that laser light is emitted through the reservoir to a predetermined area inside the reservoir or predetermined meridian point of a user's body.

In one aspect of the invention, a laser module may be coupled to a support mechanism and attached to a peripheral wall of the reservoir. The support mechanism is configured such that the laser module can be positioned either substantially parallel with the peripheral wall of the reservoir, or at an angle relative to the peripheral wall so that light can be directed at a particular meridian point of the user's body.

According to another aspect of the invention, a laser module may be coupled to a support mechanism that is attached to a peripheral wall of the reservoir, whereby the laser module is configured such that laser diodes inside the laser module are attached at an angle relative to the base of the reservoir, such as, approximately 15 degrees, and emit laser light inside the reservoir at a height of between ½ to 1 inch above the base floor of the reservoir.

According to another aspect of the invention, the laser module accommodates two laser diodes, wherein a first laser diode has a peak power of about 10 mW and a second laser diode has a peak power of about 5 mW.

According to another aspect of the invention, the laser module accommodates two laser diodes, wherein a first laser diode emits laser light that is directed to a left foot of a user and a second laser diode emits laser light that is directed to a right foot of the user, wherein the laser light emitted from the first and second laser diodes is directed to predetermined locations inside the reservoir at heights of about ½ inch to 1-inch above the base.

According to another aspect of the invention, a base floor of the reservoir is formed with at least one protrusion, wherein the protrusion is positioned to provide a pressure point on the sole of a person's foot so that pressure is applied to the Kidney meridian.

According to another embodiment of the invention, the reservoir is configured such that a disposable liner can line an inside surface of the reservoir and be removably attached from the reservoir, wherein the liner can be disposed and a new liner inserted for each person, thereby reducing the spread of bacteria from one user to the next.

It is to be understood that both the foregoing general description and the following detailed description are exemplary and explanatory and are intended to provide further explanation of the inventions as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1:
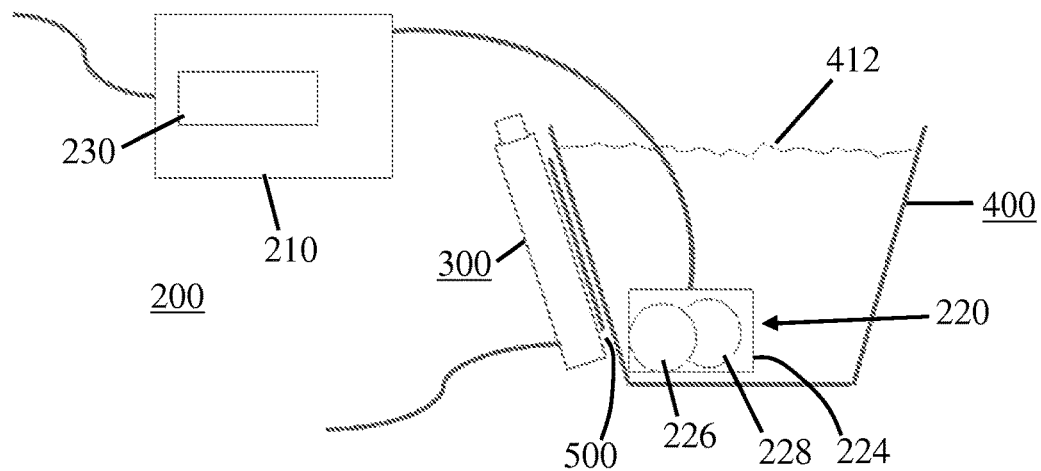
FIG. 1 is an illustration showing a block diagram of a laser ionization therapy system according to an embodiment of the invention.

FIG. 1 illustrates a laser-ionization therapy assembly 100 according to an embodiment of the invention. As shown, the laser-ionization therapy assembly 100 comprises an ion generating unit 200, a laser module 300, a reservoir 400, and a support mechanism 500.

The ion generating unit 200 comprises a power supply 210 and an electrode array 220 coupled to the power supply 210. The electrode array 220 may be comprised of replaceable electrodes mounted within a housing 224. The electrodes may comprise an anode 226 and a cathode 228. The power supply 210 is capable of delivering a low voltage direct current to the electrode array 220 and may further comprise a display screen 230 capable of displaying the voltage and amperage of a treatment power applied from the power supply 210 to the electrode array 220. The display screen 230 may be capable of displaying other information, such as an amount of time elapsed during treatment of a user. The power supply 210 may be programmed with multiple ionization treatment options, some of which may be pre-programmed and others may be custom designed for each user.

According to an embodiment of the invention, the electrode array 220 may be placed in the reservoir 400 and immersed in water contained therein. The reservoir 400 may be made of a transparent material, electrically insulative, and capable of holding water (e.g., plastic, glass, etc.). The reservoir 400 is not limited to any particular size, shape, or material.

In one aspect of the invention, the water may be provided as normal tap water. In another aspect of the invention, a predetermined amount (e.g., a half cup) mineral salts and/or a predetermined amount (e.g., about 1 psp) of liquid materials may be mixed with the water 412 to enhance the electrical conductivity characteristics of the water 412. In one aspect of the invention, the liquid materials may include magnesium with 50 types of trace materials.

In one aspect of the invention, a first ionization treatment option may result in the generation of only positive ions within a predetermined treatment time (e.g., about 30 minutes). A second ionization treatment option may result in the generation of only negative ions within the predetermined treatment time. A third ionization treatment option may result in the generation of a mix of positive and negative ions (e.g., 70% are positive and 30% are negative). A fourth ionization treatment option may result in the generation of positive ions for about 15 minutes, then negative ions for about 10 minutes, and finally positive ions for about 5 minutes. A fifth ionization treatment option may result in the generation of negative ions for about 15 minutes, then positive ions for about 10 minutes, and finally negative ions for about 5 minutes.

FIGS. 2-6 show an embodiment of the laser module 300. The laser module 300 may be programmable or non-programmable. It is understood that the laser module 300 is not limited to the particular embodiment shown.

Figure 2:
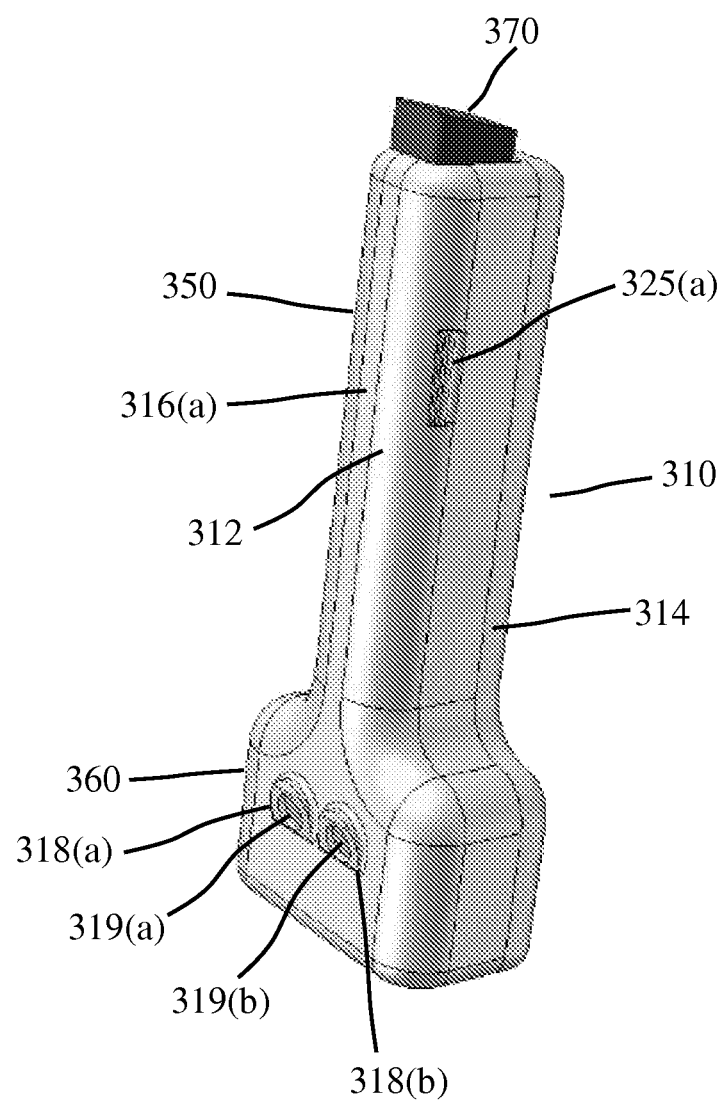
FIG. 2 is an illustration showing a front view of a laser module assembly according to an embodiment of the invention.
Figure 3:
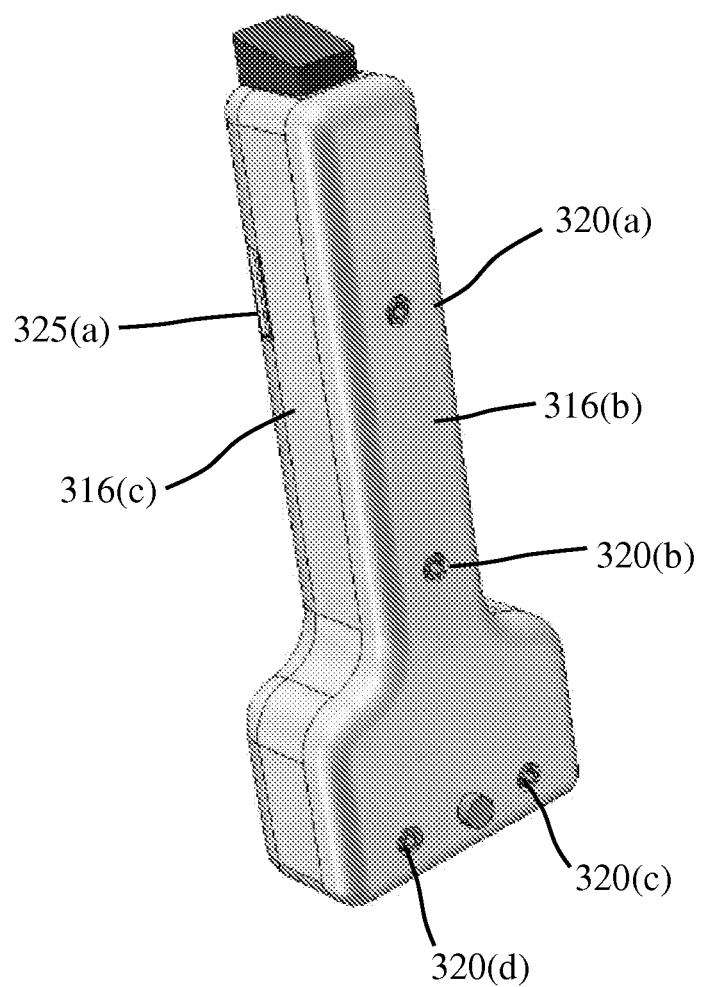
FIG. 3 is an illustration showing a rear view of the laser module assembly shown in FIG. 2.

FIGS. 2 and 3 are illustrations showing a front view and a back view of the laser module 300, respectively. As shown in FIG. 2, the laser module 300 comprises a housing 310. The housing 310 can be made of any suitable material, and is preferably injection molded of a rubber or plastic material. The housing 310 may be a unitary structure, or a multi-piece structure that allows access to the inside of the housing 310.

The laser module 300 shown is generally T-shaped. In this manner, the substantially vertical portion 350 of the housing 310 may function as a handle for the laser module 300, and the substantially horizontal portion 360 may house laser diodes 330, 335, and related components.

The housing 310 shown is a two piece structure comprising a front piece 312 and a rear piece 314. The pieces 312 and 314 may be attached together by screws 322(*a*), 322 (*b*), 322(*c*), and 322(*d*). For example, the rear piece 312 may include through holes 320(*a*), 320(*b*), 320(*c*), and 320(*d*) formed in a rear surface 316(*b*) thereof, and the front piece 314 may include corresponding inserts 324(*a*), 324(*b*), 324(*c*), and 324(*d*) formed at an inner wall 380 thereof. Accordingly, the screws 322(*a*), 322 (*b*), 322(*c*), and 322(*d*) may be inserted through the holes 320(*a*), 320(*b*), 320(*c*), and 320 (*d*) and into the inserts 324(*a*), 324(*b*), 324(*c*), and 324(*d*) thereby securing the front piece 312 and rear piece 314 together. It is understood that the pieces 312 and 314 may be affixed to each other by any known attachment method, including, for example, by a snap fit configuration, adhesive, etc.

The housing 310 includes at least one opening 318(*a*), 318(*b*), or window, formed on a front surface 316(*a*) of the laser module 300 through which laser light must emit. The embodiment shown in FIG. 2 includes a left opening 318(*a*) and a right opening 318(*b*) formed on the front surface 316(*a*) of the laser module. The opening(s) are not limited to any particular shape or size. However, the opening(s) must be large enough to allow for the laser light to pass through the housing 310. The laser module 300 may also include one or more mirrors to direct and/or focus the laser light generated by the laser diodes (not shown).

The laser module 300 may further include a lens material 319(*a*), 319(*b*) provided at each opening 318(*a*), 318(*b*), respectively. The lens material 319(*a*), 319(*b*) focuses the laser light emitted from laser diodes 330, 335. In particular, the lens material 319(*a*), 319(*b*) respectively collimate laser light emitted from laser diodes 330, 335, so that the laser light is aligned in a specific direction.

Figure 4:
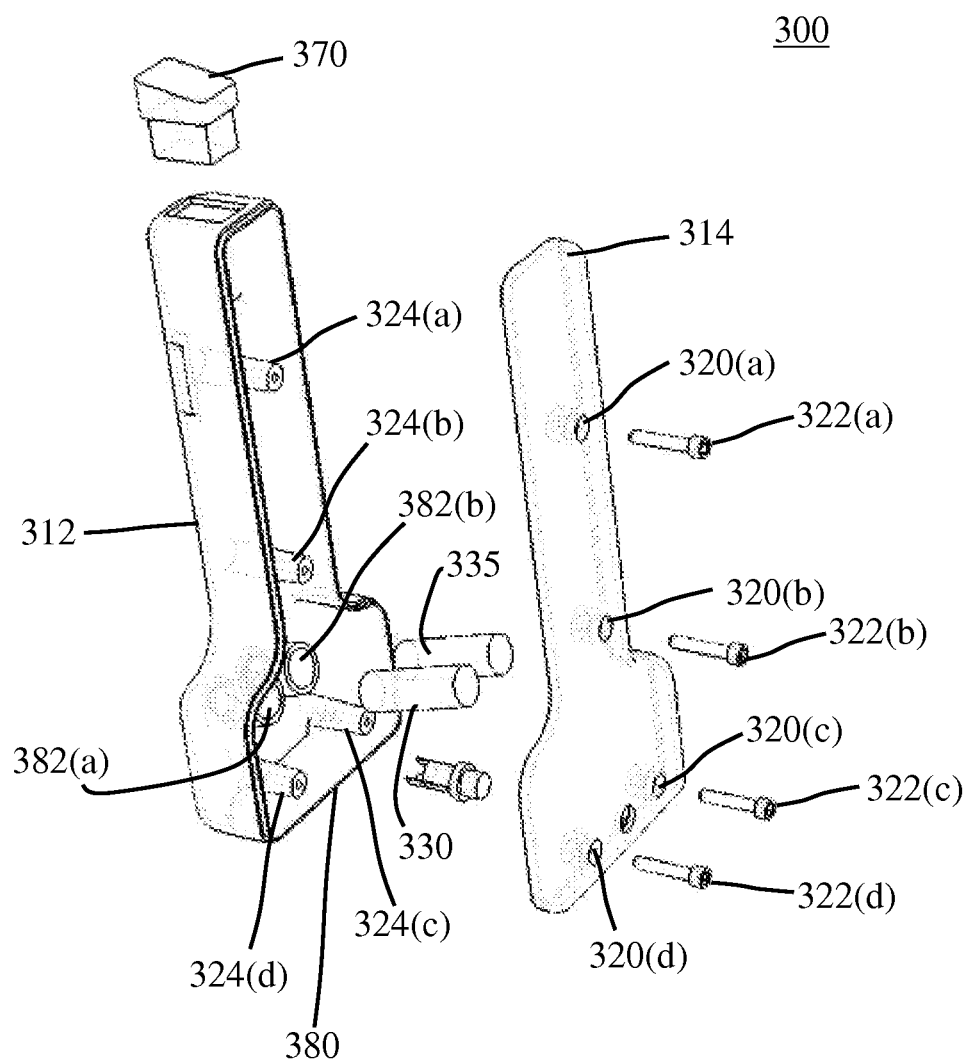
FIG. 4 is an illustration showing an exploded isometric view of the laser module assembly shown in FIG. 2.

FIG. 4 is an exploded view of the laser module 300 according to an embodiment of the invention. As shown, the laser module 300 houses laser diodes 330 and 335. The laser diodes may, for example, include AIXIZ Laser Module AH635-5-3-12, which is a 635 nm, 5 mW laser diode. There is no limit to the number of diodes that can be housed within the housing 310. For example, the housing 310 may include a single diode, or several diodes. Accordingly, each diode inside the housing 310 may emit light towards a different predetermined location.

The laser module 300 may include laser diode support structures 382(*a*), 382(*b*) that are attached or formed with an inner wall 380 of the housing 310. The laser diode support structures 382(*a*), 382(*b*) are configured to position and receive the laser diodes 330 and 335. The laser diode support structures 382(*a*), 382(*b*) may be angled such that laser light from the laser diodes 330 and 335 is directed through the openings 318(*a*), 318(*b*) of the laser module to a predetermined location. The laser diodes 330 and 335 may be secured or attached to the laser diode support structures 382(*a*), 382(*b*) by an adhesive, such as two way tape, or mechanical means. It is understood that the laser diodes 330 and 335 may be attached to the housing by other means.

Figure 5:
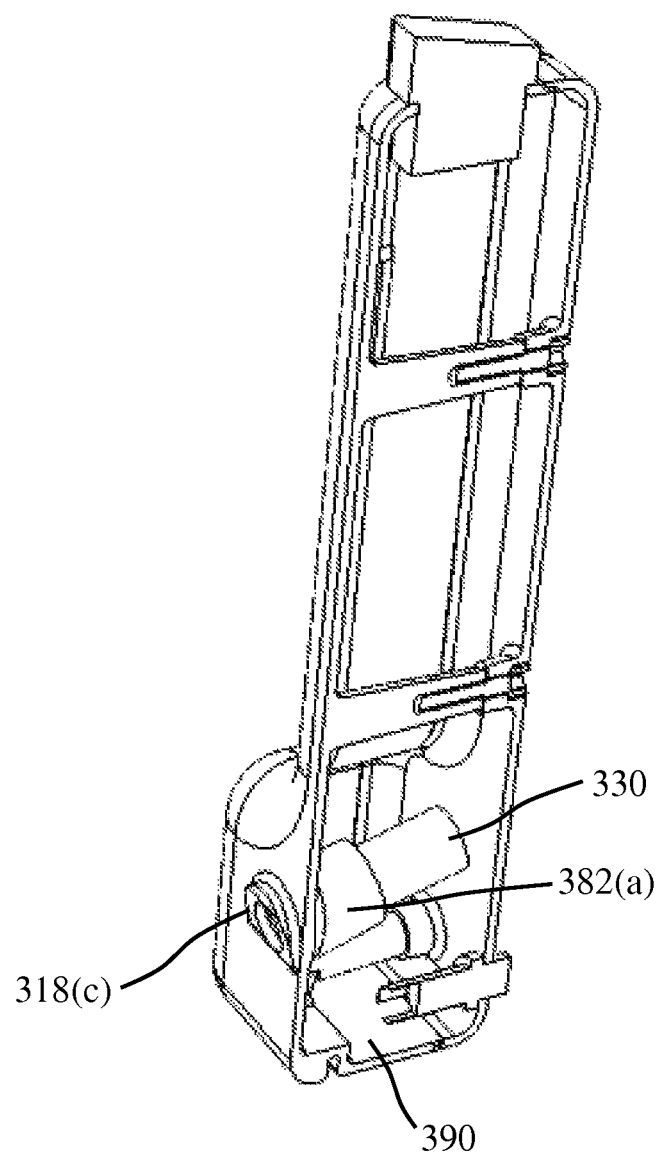
FIG. 5 is an illustration showing a sectional view of the laser module assembly shown in FIG. 2.

FIG. 5 is a sectional view of the laser module 300 shown in FIG. 4. As shown, the laser diode support structure 382(*a*) is attached to or formed with an inner wall 380 of the housing 310. The laser diode support structure 382(*a*) may be provided at an angle relative to a bottom inner surface 390 of the housing 310. For example, as shown, the laser diode support structure 382(*a*) may be angled at approximately 15 degrees relative to the bottom inner surface 390 so that the laser diode 330 attached thereto may emit laser light to a predetermined location within the reservoir 400.

Figure 6:
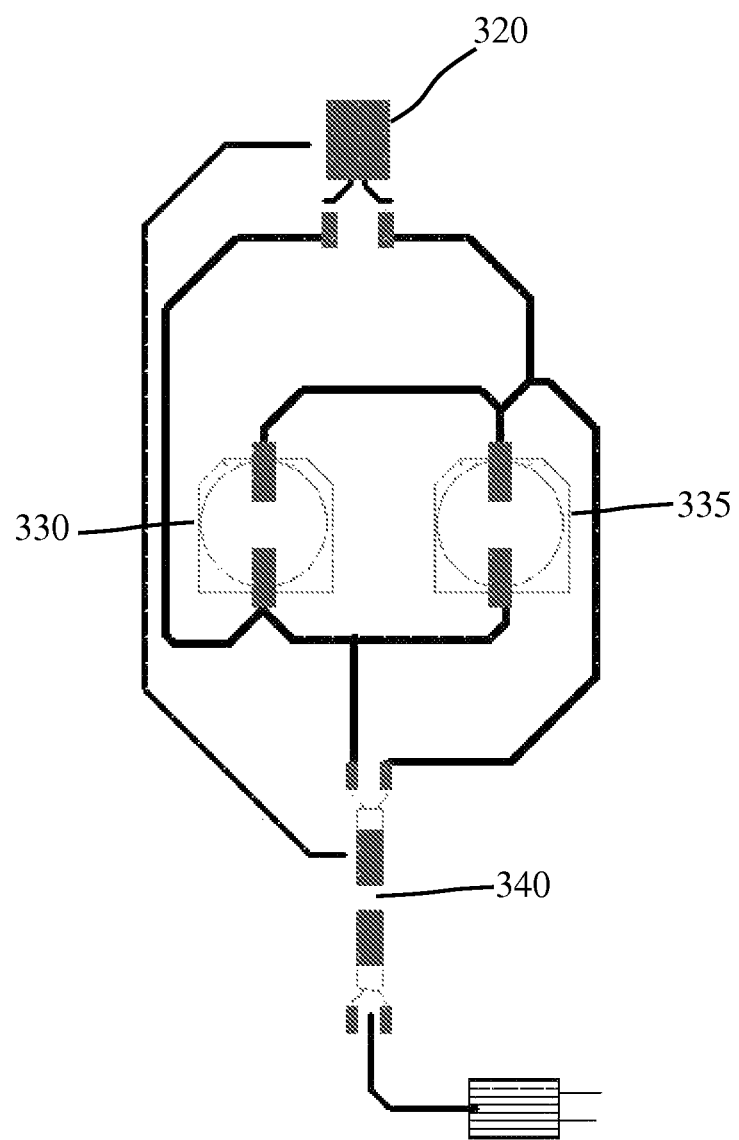
FIG. 6 is an illustration showing a wiring diagram for the laser module assembly shown in FIG. 2.

FIG. 6 is a wiring diagram for an embodiment of the laser module 300. As shown, the laser module 300 comprises a left laser diode 330 and a right laser diode 335. The lasers diodes 330 and 335 generate substantially coherent light (e.g., laser light). The laser diodes 330 and 335 are affixed and positioned inside of the housing 310 such that substantially all of the laser light generated by the laser diodes 330 and 335 exits the laser module 300 through openings 318(*a*) and 318(*b*).

In one embodiment of the invention, the laser module 300 generates light at a wavelength of between about 630 and 640 nm and at a power of about 10 mW or less, preferably about 5 mW or less. In another embodiment of the invention, light generated by the laser module 300 has a wavelength of substantially about 635 nm. In one aspect of the invention, the generated light may be directed toward a person's body as a substantially continuous beam of light or a pulsed beam having a predetermined frequency. In one aspect of the invention, pulsing of the light toward the user may alleviate pain and increase circulation within the body, stimulate glands, etc. In another aspect of the invention, the frequency at which light directed toward the user is pulsed may be determined based on results of a second muscle testing procedure and the location of the user's body where the light is to be directed.

The laser module 300 may include an on/off switch 370. The on/off switch 370 is preferably located at the top surface 316(*e*) of the housing 310, but may be located anywhere on the laser module 300. The on/off switch 370 may be a toggle switch, such as Cherry KRE2ANA1BBD. However, the invention is not limited to any particular type of switch for the actuation of electrical supply to the laser module 300. For example, a rocker type switch, toggle switch, push button switch, or the like may be used.

The laser module 300 may be powered by AC power such that it does not operate on battery power. For example, the laser module 300 may include a power plug electrical connector 340 for removably connecting the laser module 300 to an AC power supply.

Figure 7:
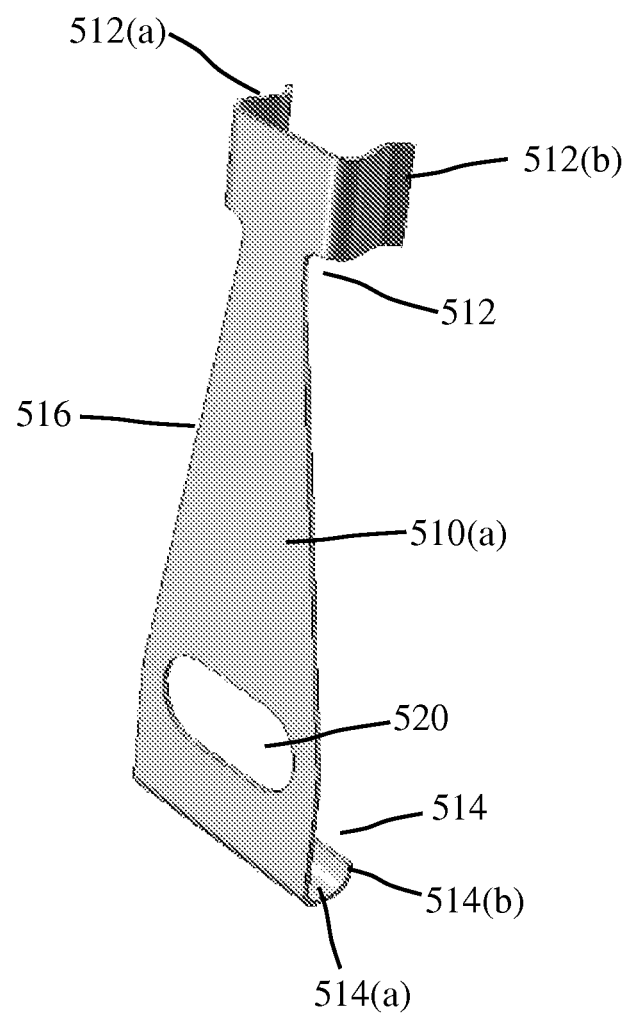
FIG. 7 is an illustration showing a front isometric view of a support mechanism according to an embodiment of the invention.
Figure 8:
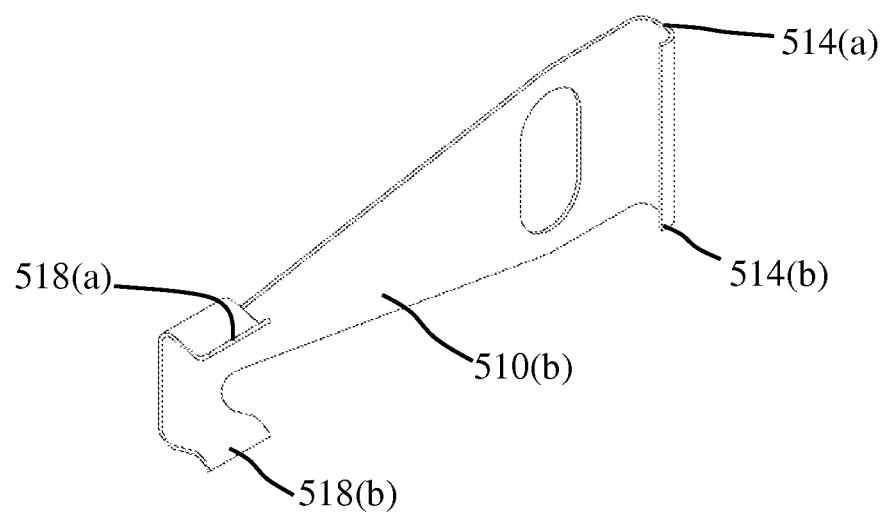
FIG. 8 is an illustration showing a back isometric view of the support mechanism shown in FIG. 7.

FIGS. 7 and 8 are illustrations showing a front view and a rear view of a support mechanism 500, respectively, according to an embodiment of the invention. The support mechanism 500 is provided to support and/or position the laser module 300 with the reservoir 400 so that the laser light emitted from the laser module 300 can be directed to a predetermined location within the reservoir 400. The support mechanism 500 may be formed from a 3000-Series Aluminum Alloy Sheet. However, it is understood that the support mechanism 500 can be made of any suitable material, such as metal or plastic, and is not limited to any particular geometric shape.

As shown, the support mechanism 500 includes a front surface 510(*a*) and a rear surface 510(*b*). The front surface 510(*a*) is the surface that is proximate a peripheral sidewall of the reservoir 400 when the support mechanism is attached to the reservoir. The rear surface 510(*b*) is the surface of the support mechanism 500 that is proximate to the housing 310 when the laser module is attached to the support mechanism 500. The support mechanism 500 includes a top end 512 and a bottom end 514. The top and bottom ends 512 and 514 are located at opposite ends of the support mechanism 500. The support mechanism 500 may extend along a major axis of the laser module 300 (see, e.g., FIGS. 14 and 15) when the laser module 300 is attached thereto.

Preferably, the support mechanism 500 is shaped such that planar portion 516 of the support mechanism 500 is substantially parallel with the housing 310 and does not extend outside of the profile of the housing 310. For example, the planar portion 516 has a flare shape and generally follows the shape of the laser module 300.

As shown, the bottom end 514 of the support mechanism 500 may be configured to hold a bottom portion 324 of the laser module 300. In particular, the bottom end 514 may form a receiving portion to receive and secure the bottom portion 324 of the laser module 300. The bottom end 514 may comprise a substantially U-shaped flange having a bottom surface 514(*a*) and a coupling member 514(*b*), such as a hook.

The aforementioned top end 512 of the support mechanism 500 may be configured to hold an upper portion 326 of the laser module 300. The upper portion 326 is not limited to any particular area of the laser module, but instead refers to a portion of the laser module 300 that is above the bottom portion 324 with respect to the major axis of the laser module 300. As shown, the upper portion 326 may include a first projection 512(a) and a second projection 512(b). The first projection 512(a) may extend from a left side of the support mechanism 500, and the second projection 512(b) may extend from a right side of the support mechanism 500. The first and second projections 512(a) and 512(b) each include an outwardly extending coupling member 518(a) and 518(b), respectively. The coupling members 518(a) and 518(b) may be flanges.

The support mechanism 500 may include window or opening 520. The opening 520 is dimensioned to receive laser light emitted from the laser module 300. More particularly, the opening 520 is dimensioned and positioned to receive light emitted through openings 318(a), 318(b) of the laser module 300 when the laser module 300 is coupled with the support mechanism 500. For example, the opening 520 may be a single, substantially oval shaped opening that is aligned and dimensioned so that laser light emitted from the laser module 300 can be transmitted there through and directed to a predetermined location, e.g., approximately ¾ inch to 1 inch above an interior base of the reservoir 400 so that the laser light will contact a person's large toe. The opening 520 is not limited to any particular size or shape.

Figure 9:
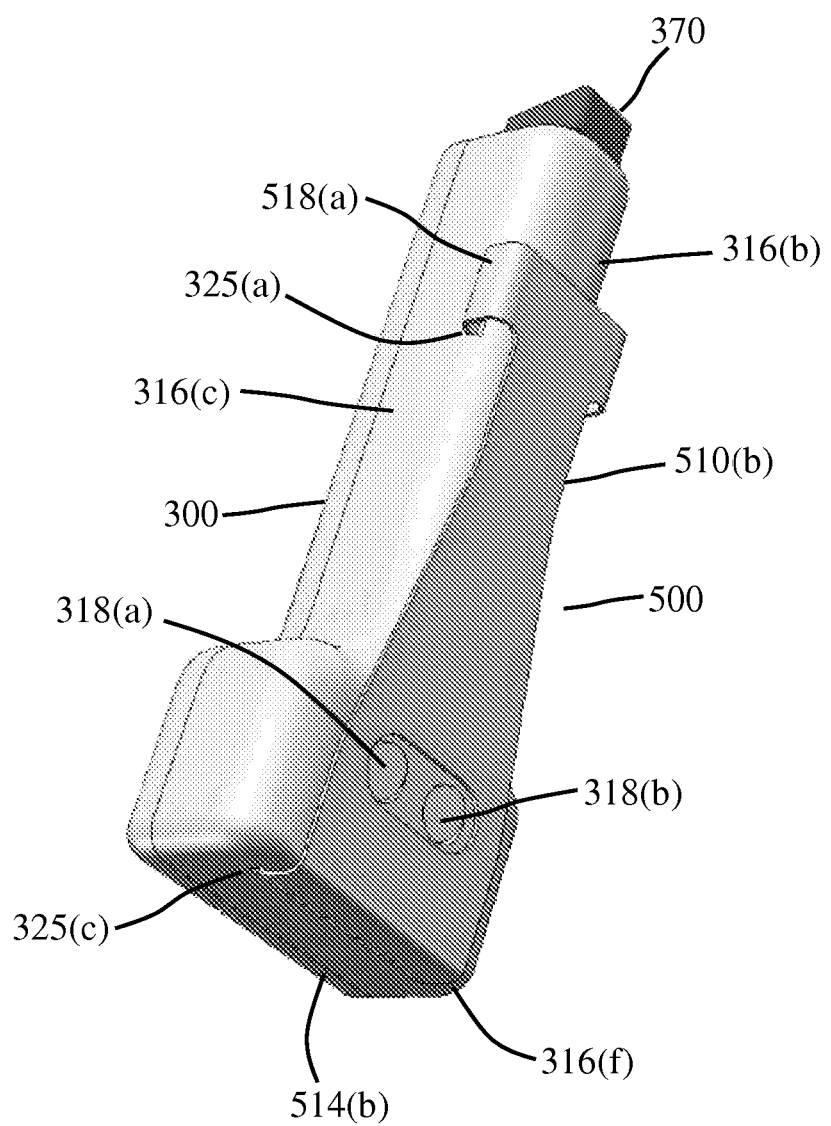
FIG. 9 is an illustration showing a laser module coupled with a support mechanism according to an embodiment of the invention.

FIG. 9 shows the support mechanism 500 coupled with the laser module 300 according to an embodiment of the invention. As shown, when the laser module 300 is coupled with the support mechanism 500, the planer portion 516 of the support mechanism 500 is proximate to and substantially parallel with the laser module 300. The first projection 512(a) and the second projection 512(b) are detachably coupled with right and left sides of the laser module 300, respectively. In particular, coupling members 518(a), 518(b) are inserted in and detachably coupled with coupling grooves 325(a), 325(b) that are formed at side surfaces 316(c), 316(d) of the laser module 300, respectively. The coupling grooves 325(a), 325(b) may extend in a substantially vertical direction along the side surfaces 316(c), 316 (d). It is understood that the coupling members 518(a) and 518(b) may be secured to the laser module 300 by other mechanical means, such as tension or adhesion.

The bottom surface 514(a) of the support mechanism 500 extends below the laser module 300. The coupling member 514(b) of the support mechanism 500 is inserted in and detachably coupled with a coupling groove 325(c) formed at the bottom surface 316(f) of the laser module 300 (see, e.g., FIG. 14). The coupling groove 325(c) may extend substantially across the bottom surface 316(f). It is understood that the coupling member 514(b) may be secured to the laser module 300 by other mechanical means, such as tension or adhesion.

Figure 10A:
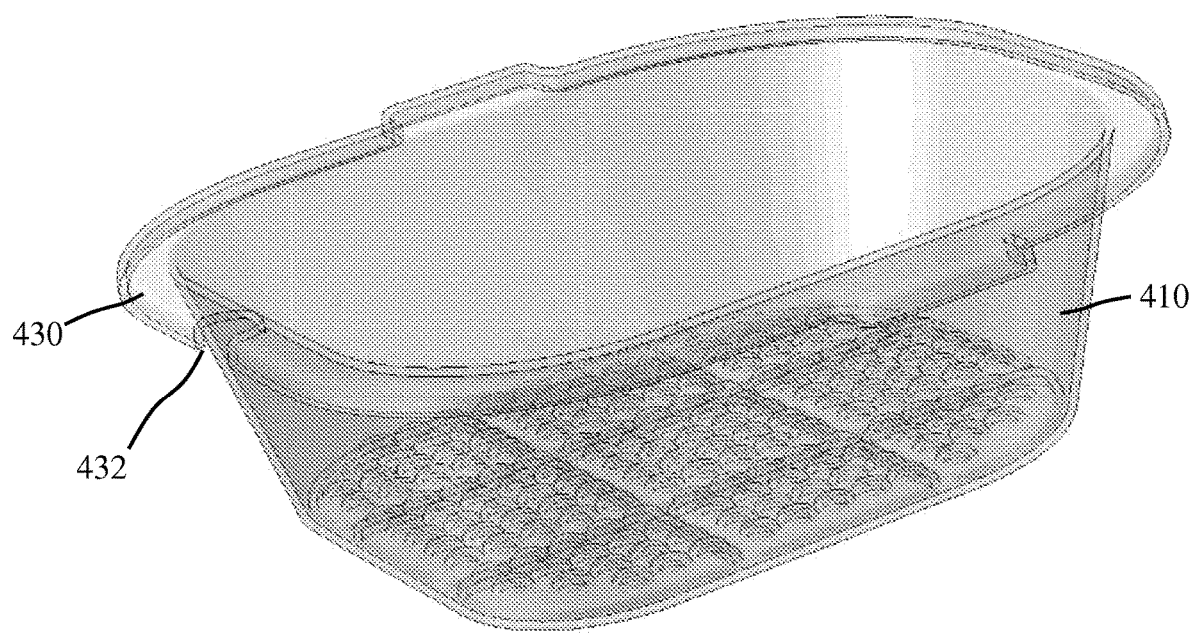
FIG. 10(A) is an illustration showing an isometric view of a reservoir according to an embodiment of the invention.
Figure 10B:
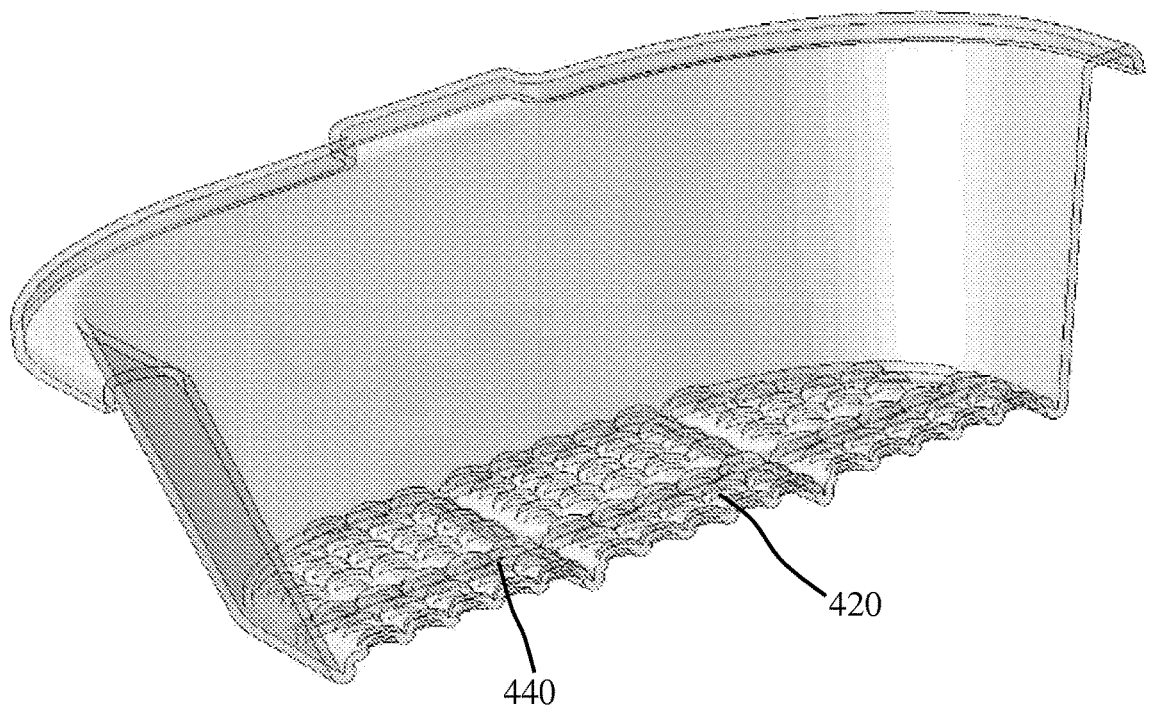
FIG. 10(B) is an illustration showing a sectional view of the reservoir shown in FIG. 10(A)

FIGS. 10(A) and 10(B) are illustrations of a reservoir 400 according to an embodiment of the invention. As shown, the reservoir 400 includes a cavity defined by a peripheral wall 410 and a base floor 420. The peripheral sidewall 410 may be substantially perpendicular to the base floor 420, or angled. For example, the peripheral sidewall may flare out approximately 15 degrees from bottom to top.

The reservoir 400 may be made of a material or have a configuration that allows laser light to pass through. The reservoir 400 may be made entirely or partly of a transparent material, such as, for example a clear plastic material.

Additionally, the reservoir 400 may include a transparent portion adjacent to the opening 520 in the support mechanism 500 when the support mechanism is attached to the reservoir 400.

The reservoir 400 may further include a top rim 430. The top rim 430 may extend outward from an exterior surface of the peripheral wall 410. The top rim 430 may include a cut out portion 432. The cut out portion 432 may be positioned to receive a portion of the laser module 300. The cut out portion 432 may also function as an alignment means for the bracket structure 500. The on/off switch 370 of the laser module 300 may be positioned at least partially within the cut out portion 420. Additionally, the top rim 430 may extend outward from the peripheral wall 410 at least as far as the front surface 316(a) of the laser module 300.

As shown in FIG. 10(B), the reservoir 400 may include at least one bump 440 or protrusion formed on the base floor 420 to perform acupuncture therapy. Preferably, as shown, the base floor 420 includes a plurality of bumps 440. The bumps 440 may be integrally formed with the reservoir, or provided on a separate material that may be set on the base floor 420 of the reservoir 400, e.g., a floor mat. The bumps 440 are shaped and positioned to function as pressure points on the bottom of a person's foot for foot acupuncture therapy.

Figure 22:
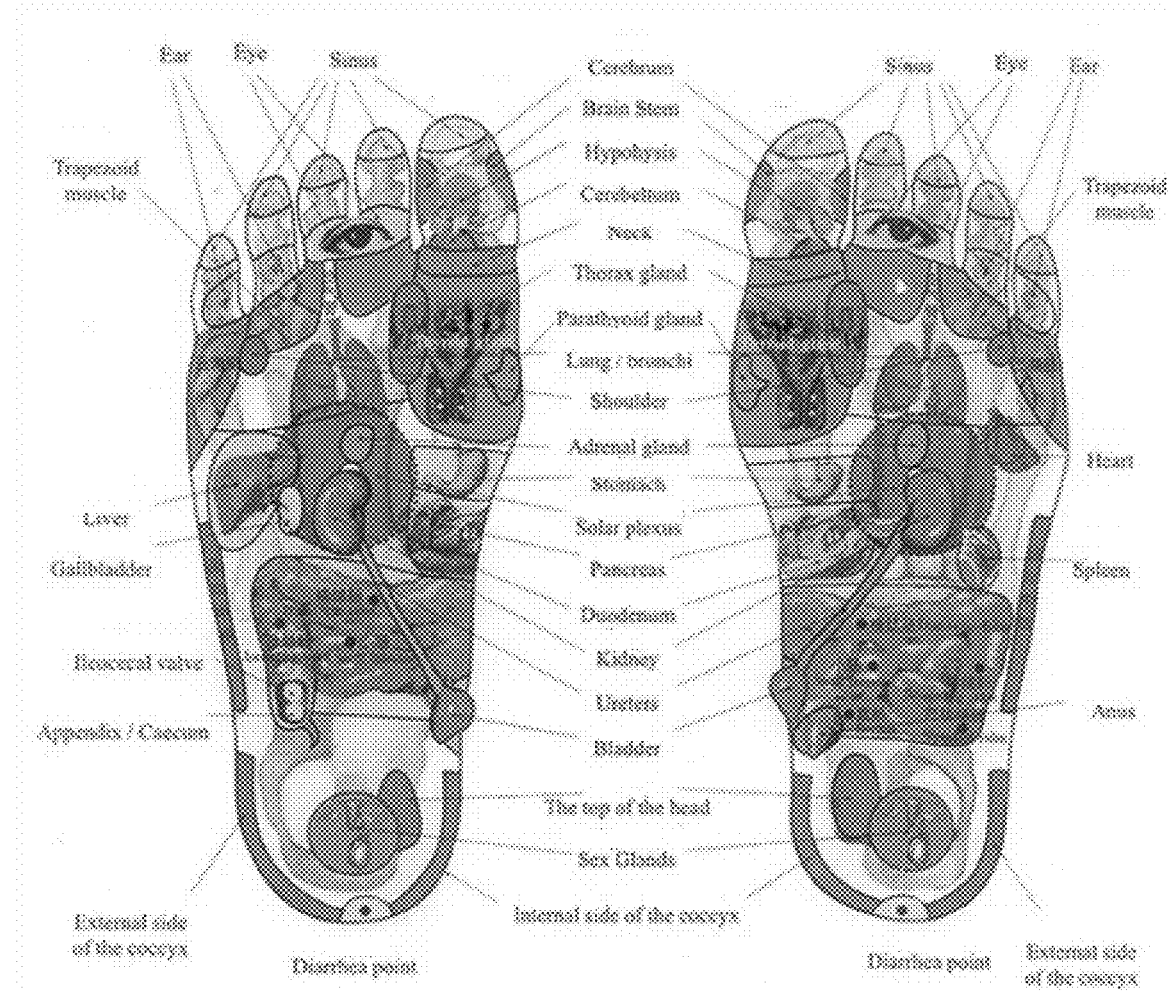
FIG. 22 is a chart for laser light therapy and pressure points for a person's foot.

Preferably, the bumps 440 are positioned to press against the Kidney 1 acupuncture point on the bottom of a person's foot. Kidney 1 is the lowest acupuncture point on the entire body and an entry point into the kidney meridian. As shown in FIG. 22, which is a chart for laser light therapy and pressure points for a person's foot, the Kidney 1 acupuncture point is located on the sole of a person's foot, in the depression when the foot is in plantar flexion, approximately at the anterior third and the posterior two-thirds of the line from the web between the second and third toes to the back of the heel. The Kidney 1, known as "Gushing Spring" is known to drain excess energy from an upper part of the body, especially the head. In other words, when there is excess energy in the upper part of the body, it can cause symptoms such as anxiety, headaches, insomnia, and panic attacks. Because Kidney 1 has such a strong downward moving action, acupuncture therapy on the Kidney 1 point is known to quickly remove these symptoms.

Figure 11:
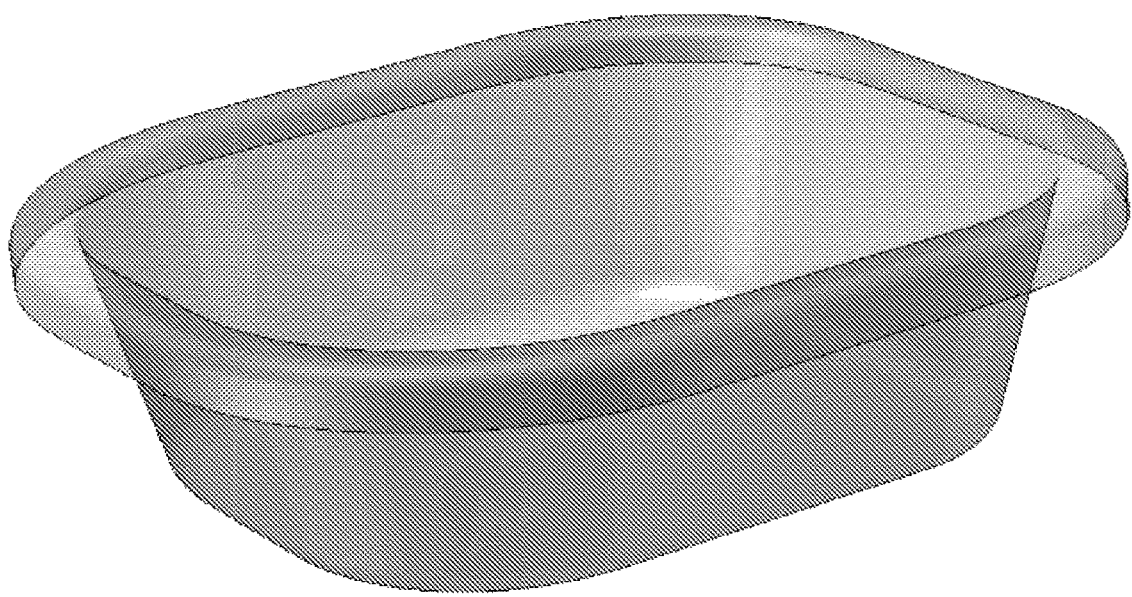
FIG. 11 is an illustration showing an isometric view of a liner according to an embodiment of the invention.

FIG. 11 is an illustration of a liner 600 according to an embodiment of the invention. The reservoir 400 may be configured to receive the removable liner 600. The liner may affixed to the upper rim portion 430 to secure it in place. The liner 600 may be a sanitary plastic liner that is removable and disposable. The liner 600 is preferably sized and configured to fit into the inside of the reservoir 400 and substantially conform to the peripheral wall 410 and interior base 420, and made of a material that is liquid impermeable and permits laser light to pass through. For example, the liner 600 may be formed of a translucent plastic thermoformed type material having a thickness that is less than 0.001 inch.

The liner 600 may be placed inside the reservoir 400 and then filled with a liquid material for use by a single person. After such use, the liner and its contents may be discarded and a new liner 600 placed in the reservoir 400 for a subsequent user. Thus, any risk of cross contamination is substantially reduced.

Figure 12:
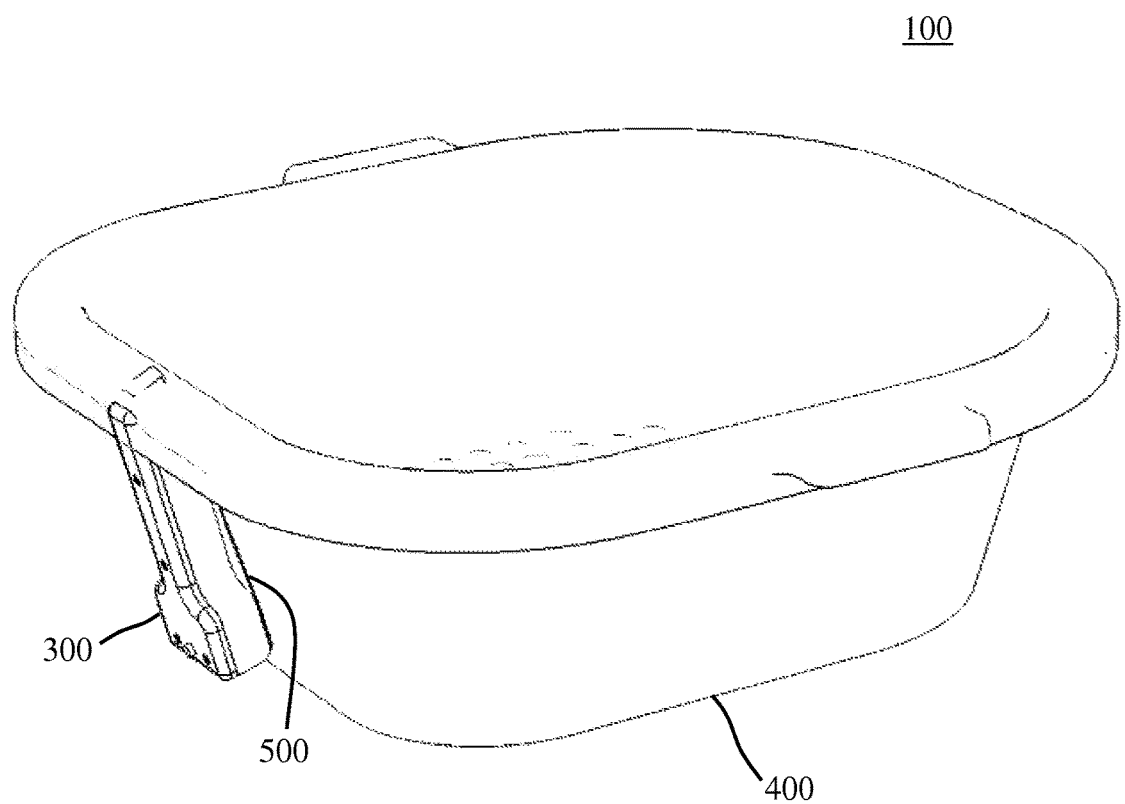
FIG. 12 is an illustration showing an isometric view of a laser ionization therapy assembly according to an embodiment of the invention.

FIGS. 12-15 are illustrations of the laser ionization therapy assembly 100 according to an embodiment of the invention. FIG. 12 is an isometric view of the assembly 100. As shown, the laser module 300 is coupled with support mechanism 500 and the support mechanism 500 is attached to a peripheral sidewall 410 of the reservoir 410. The support mechanism 500 is preferably attached at a center portion of the peripheral sidewall. This configuration allows laser light emitted from the laser module 300 to be directed to a predetermined location inside of the reservoir 400. Accordingly, the configuration provides for a generally hands free operation of the laser module 300 during a laser ionization therapy session.

Figure 13:
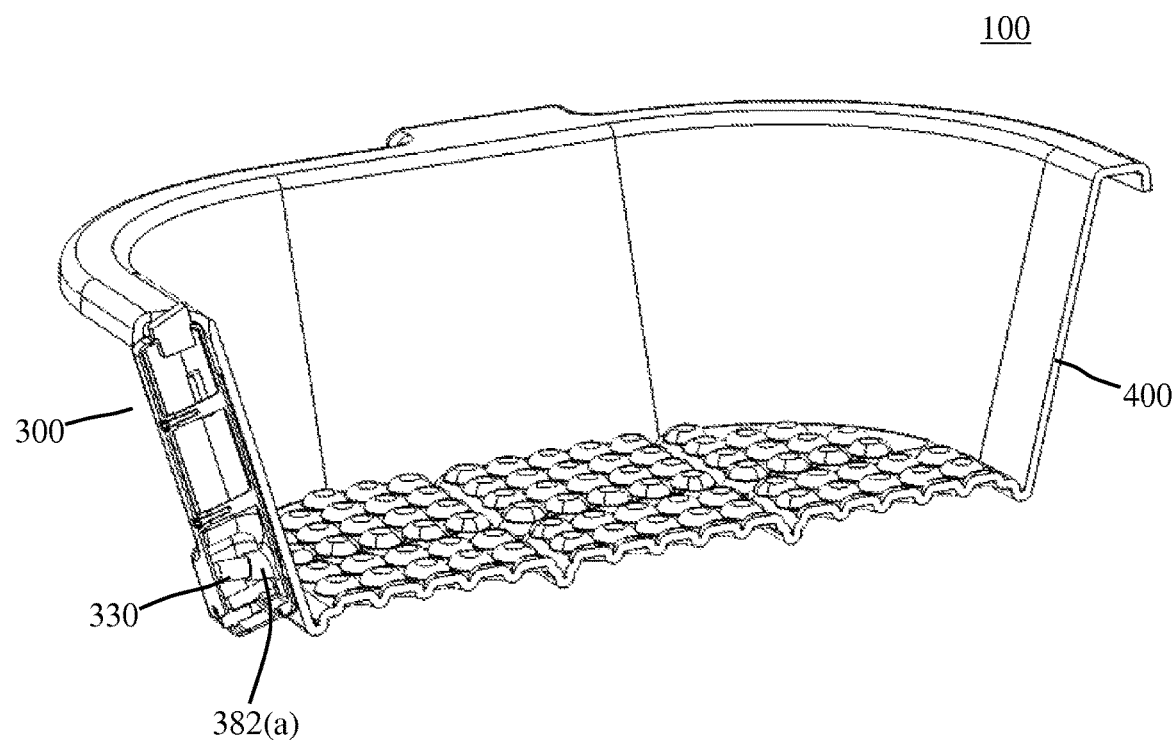
FIG. 13 is an illustration showing a sectional view of the laser ionization therapy assembly shown in FIG. 12.

FIG. 13 is a sectional view of the assembly shown in FIG. 12. As shown, the support mechanism is attached flush with the peripheral sidewall 410. The laser diodes 330, 335 are fixedly angled with respect the peripheral sidewall 410 such that laser light is emitted to a predetermined location within the reservoir 400. The support mechanism 500 may be attached to a substantially planar portion of an exterior surface of the peripheral wall 410. Preferably, the support mechanism 500 is attached to the peripheral sidewall 410 at a height such that the laser diodes 330, 335 are positioned approximately 1.5 inches to 2 inches above the base floor 420. For example, the laser diodes 330, 335 may be positioned approximately 1.7 inches above the base floor 420.

The support mechanism 500 may be attached to the reservoir 400 by any suitable means, e.g., adhesive material, tape, glue, Velcro, mechanical clips, etc. According to one aspect of the invention, a double sided bonding tape is used to attach the back surface 510(*b*) of the support mechanism 500 to the peripheral wall 410. According to another embodiment of the invention, the support mechanism 500 may be clasped to a top rim 430 of the reservoir 400. The support mechanism 500 may also be permanently attached to the reservoir. Alternatively, the support mechanism 500 may be integrally formed as part of the reservoir 400 such that the reservoir 400 and support mechanism 500 comprise a unitary structure.

Accordingly, when the support mechanism 500 is attached to the reservoir 400 and coupled to the laser module 300, the laser diodes 330 and 335 are positioned so that the laser light can be emitted to a predetermined location within the reservoir 400. For example, the left laser diode 330 may be configured to emit laser light towards a large toe on a person's left foot within the reservoir 400, and the right laser diode 335 may be configured to emit laser light toward a large toe on the person's right foot within the reservoir 400.

Figure 14:
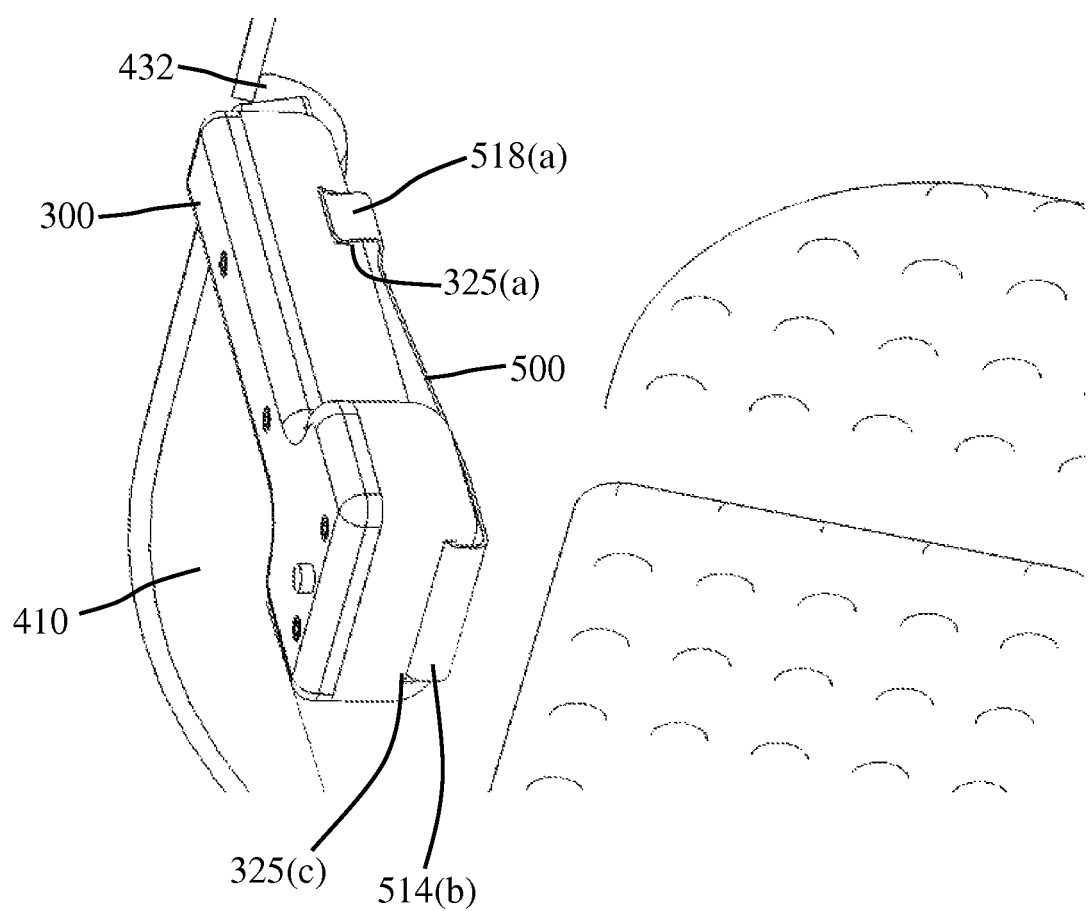
FIG. 14 is an illustration showing a close up side view of the laser ionization therapy assembly shown in FIG. 12.

FIG. 14 is a close up view of the laser ionization therapy assembly 100 shown in FIG. 12. As shown, the laser module 300 is coupled with the support mechanism 500, and the support mechanism is attached to a peripheral sidewall 410 of the reservoir 400. The top rim 430 of the reservoir 400 is formed with a cut out portion 432. The cut out portion 432 is preferably formed in the top rim 430 at a center of the corresponding the peripheral sidewall. The on/off switch 370 of the laser module 300 may be positioned at least partially within the cut out portion 420.

Figure 15:
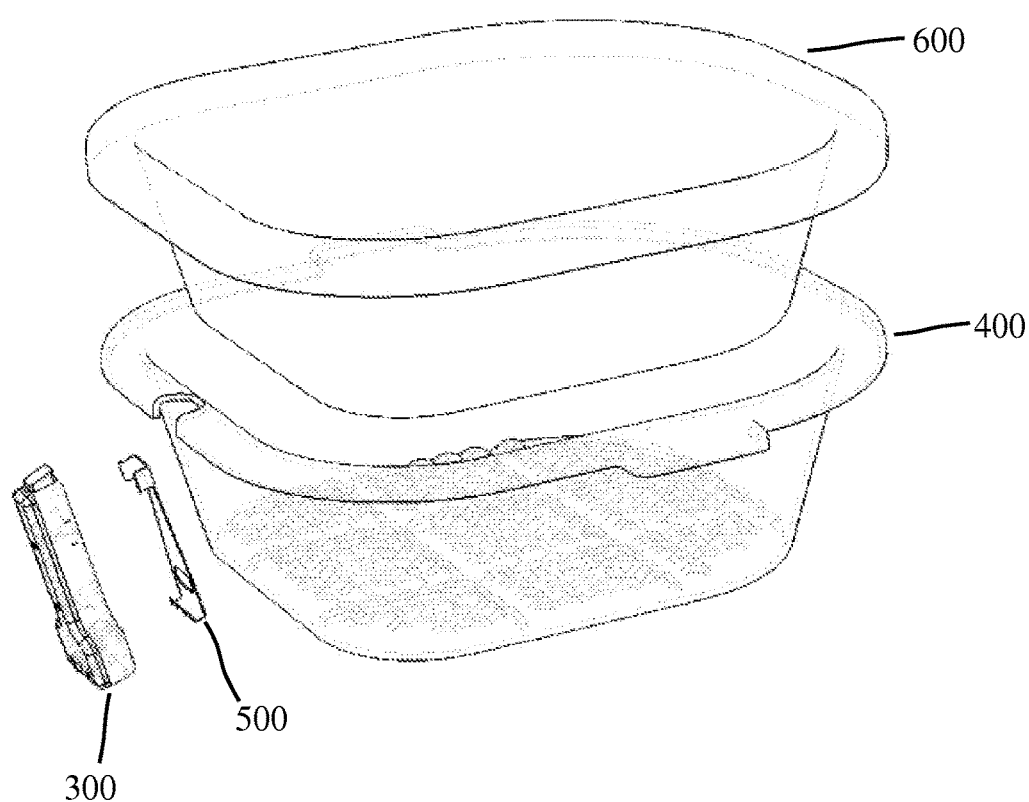
FIG. 15 is an illustration showing an exploded view of a laser ionization therapy assembly according to an embodiment of the invention.

FIG. 15 is an exploded view of the laser ionization therapy assembly 100 shown in FIG. 12. As shown, the laser module 300 is detachably coupled with a support mechanism 500. The support mechanism 500 is attached to a peripheral sidewall 410 of the reservoir 400. The support mechanism 500 may be aligned with respect to a cut out 432 that may be formed in the top rim 430. The reservoir 400 may be configured to receive a liner 600. The liner 600 may be shaped to substantially conform with an interior of the reservoir 400.

FIGS. 16-19 show a laser ionization therapy assembly 1000 according to another embodiment of the invention.

Figure 16:
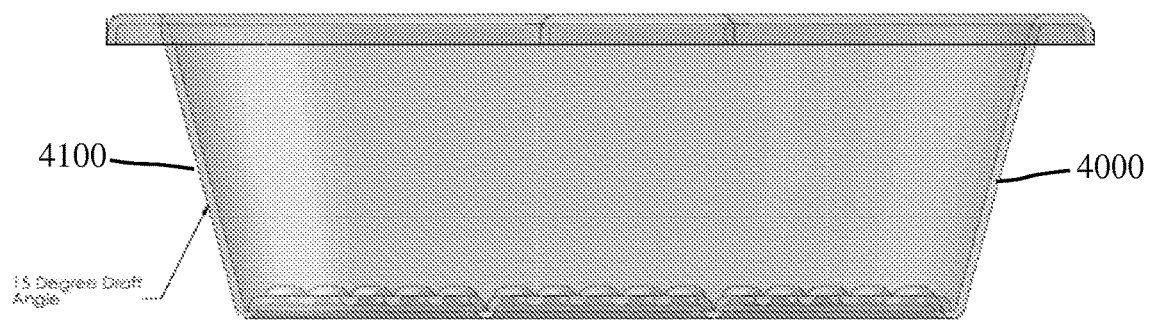
FIG. 16 is an illustration showing a side view of a reservoir according to another embodiment of the invention.
Figure 17:
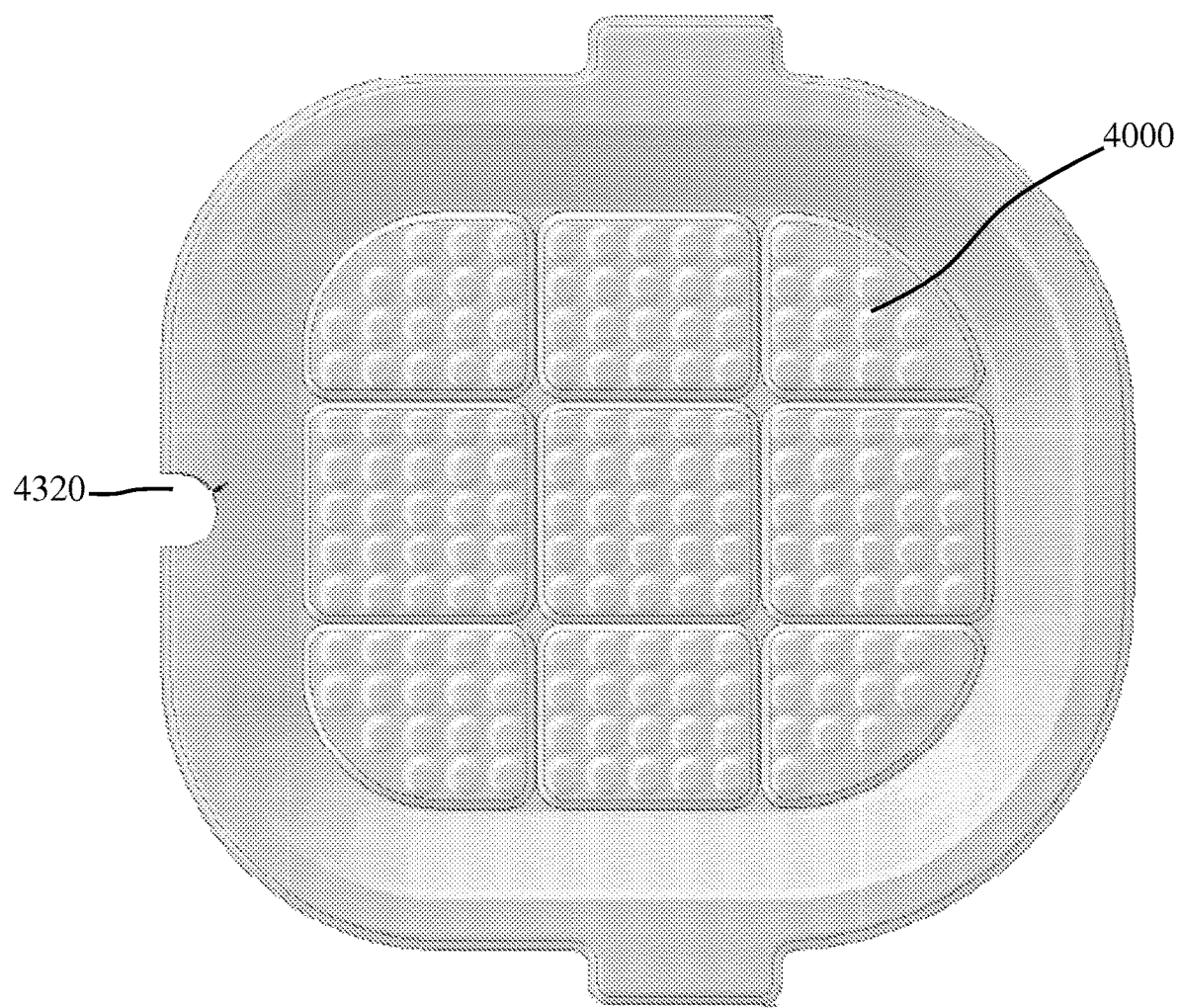
FIG. 17 is an illustration showing a top view of the reservoir shown in FIG. 16(A)

For example, FIGS. 16 and 17 show a side and top view of a reservoir 4000, respectively. The reservoir 4000 includes a peripheral sidewall 4100 that flares out at approximately a 15 degree angle from a base floor 4200. The reservoir 4000 includes a cut out portion 4320 to receive a portion of the laser module 3000 that is formed at a center of the top rim 4300. The reservoir 4000 may be formed from a clear plastic material that is approximately 0.250" thick.

Figure 18:
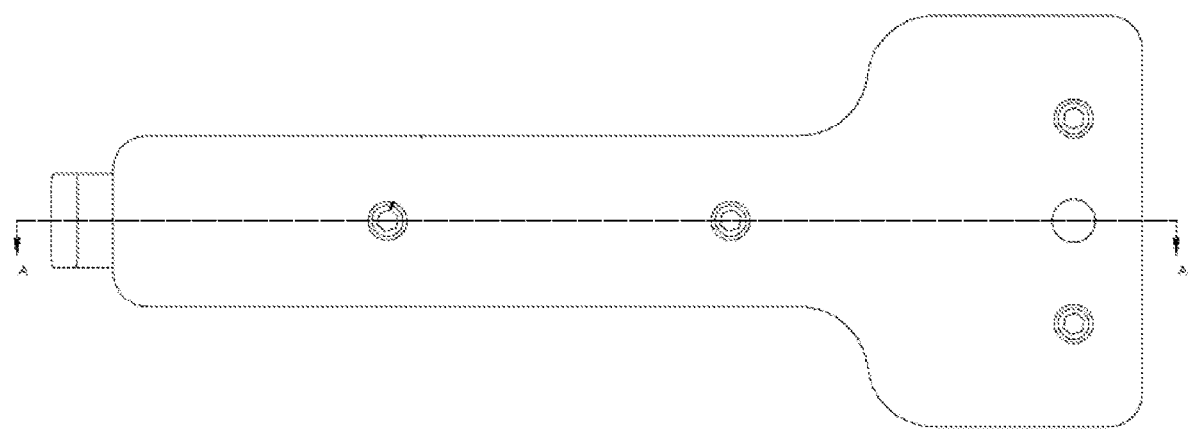
FIG. 18 is an illustration showing a laser module assembly according to another embodiment of the invention.
Figure 19:
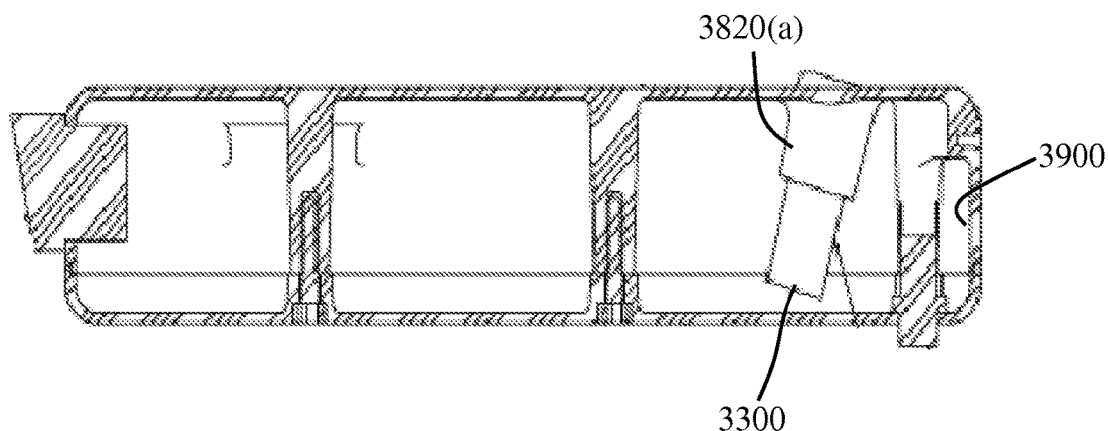
FIG. 19 is an illustration showing a sectional view of the laser module assembly shown in FIG. 17(A).

FIGS. 18 and 19 show a rear view and a sectional view of a laser module 3000. As shown, the laser module 3000 includes a laser diode support structure 3820(*a*) that is angled at approximately 15 degrees relative to a bottom inner surface 3900 of the laser module 3000. Accordingly, when a laser diode 3300 is attached to the laser diode support structure 3820(*a*), the laser diode 3300 may emit laser light to a predetermined location within the reservoir 4000, e.g., approximately ½ inch to 1 inch above a base floor 4200 of the reservoir 4000. The laser module 3000 includes an opening 3180(*a*) formed therein that is positioned to correspond with the laser diode 3300. For example, the opening 3180(*a*) may be positioned approximately 1.2 inches above a bottom exterior surface of the laser module 3000. The laser module 300 generates light at a wavelength of between about 630 and 640 nm, preferably about 635 nm, and at a power of about 10 mW or less, preferably about 5 mW or less.

Figure 20:
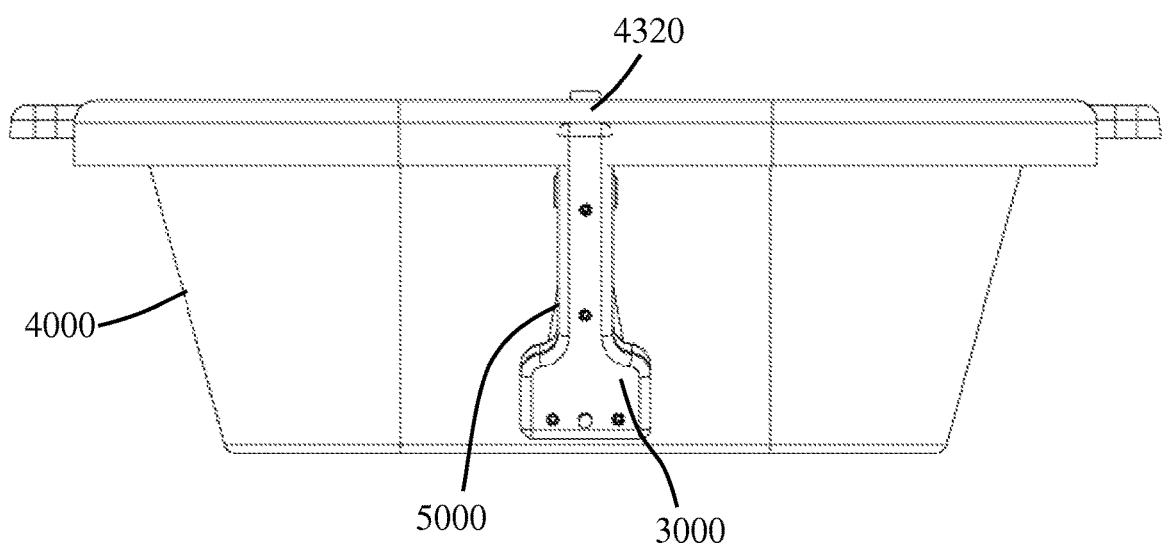
FIG. 20 is an illustration showing a front view of a laser ionization therapy assembly according to another embodiment of the invention.
Figure 21:
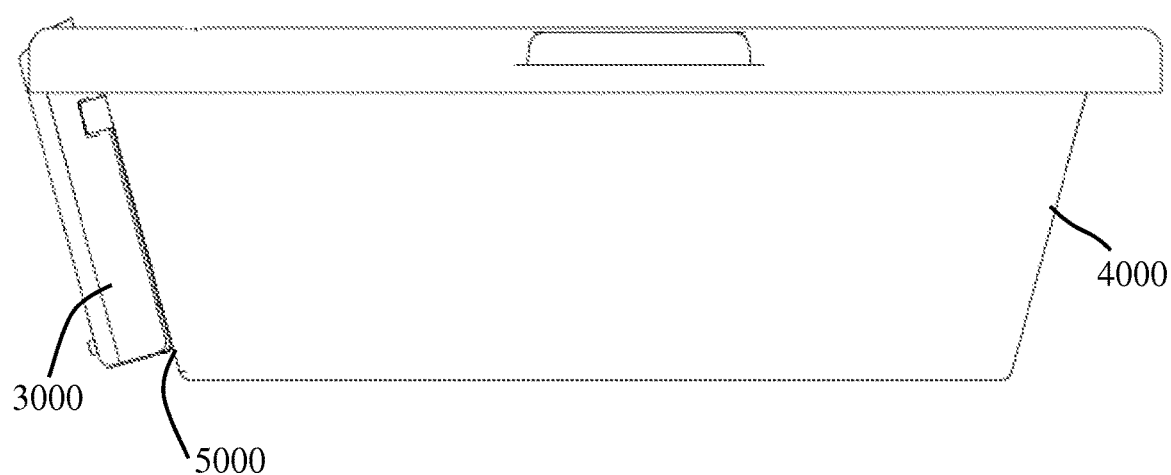
FIG. 21 is an illustration showing a side view of the laser ionization therapy assembly shown in FIG. 20.

FIG. 20 shows the laser module 3000 and support mechanism 5000 coupled together, and the support mechanism 5000 attached to the peripheral sidewall 4100 of the reservoir 4000. As shown, the support mechanism 5000 is attached at substantially a center point of the distance across the peripheral sidewall 4100. A portion of the support mechanism extends through the cut out portion 4320. FIG. 21 is a side view of the configuration shown in FIG. 20. As shown, the laser module 3000 is attached to the reservoir (via the support mechanism 5000) such that a bottom exterior surface of the laser module is ½ inch above a base floor 4200 of the reservoir 4000. Accordingly, the laser diode 3500 is positioned approximately 1.7 inches above a base floor 4200 of the reservoir, and angled at approximately 15 degrees with respect to the peripheral sidewall 4100, such that the laser light can be directed to the predetermined location within the reservoir that is about ½ inch to 1-inch above the base floor 4200. This configuration provides for a generally hands free operation of the laser module 3000 during a laser ionization therapy session.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A laser ionization therapy assembly, comprising:
a reservoir configured to hold water, the reservoir defined by a peripheral wall and a base; and
a laser module detachably coupled with the peripheral wall of the reservoir, the laser module having a first laser diode disposed therein which emits laser light having a wavelength that is greater than or equal to 630 nm and less than or equal to 640 nm and has a peak power that is 10 mW or less, the laser module arranged so that the laser light is directed inside the reservoir at a height of less than or equal to 1 inch above the base.

2. The assembly of claim 1, wherein the first laser diode is angled at 15 degrees relative to the peripheral wall.

3. The assembly of claim 2, wherein the laser module is positioned such that the first laser diode is positioned between 1.5 and 2.0 inches above the base.

4. The assembly of claim 1, wherein the wavelength of the laser light emitted from the first laser diode is 635 nm or less and the peak power is 5 mW or less.

5. The assembly of claim 1, further comprising a second laser diode,
- wherein the first laser diode is configured to emit laser light that is directed to a left foot of a user,
- wherein the second laser diode is configured to emit laser light that is directed to a right foot of the user,
- wherein the laser light emitted from the second laser diode is directed inside the reservoir at a height of between ½ inch to 1-inch above the base.

6. The assembly of claim 5, wherein the laser light emitted from the first laser diode has a peak power of 10 mW or less and the laser light emitted from the second laser diode has a peak power of 5 mW or less.

7. The assembly of claim 1, further comprising an ion generating unit that includes an electrode array in the reservoir, wherein the ion generating unit alternately produces positive ions and negative ions.

8. The assembly of claim 1, wherein the base of the reservoir includes a protrusion positioned to press against the Kidney 1 acupuncture point located on a bottom of a user's foot.

9. The assembly of claim 1, further comprising a liner that is sized to fit inside the reservoir and substantially conform to the peripheral wall and base, wherein the liner is made from a translucent plastic thermoformed type material.

10. The assembly of claim 1, wherein the laser module is powered by alternating current.

11. The assembly of claim 1, wherein the laser module comprises a second laser diode,
- wherein the peak power of the first laser diode is 10 mW or less and the peak power of the second laser diode is 5 mW or less.

12. The assembly of claim 1, further comprising a support device to support the laser module when the laser module is coupled to the reservoir.

13. The assembly of claim 12, wherein the support device is integrally formed with the peripheral wall of the reservoir.

14. The assembly of claim 12, wherein the support device is attached to the peripheral wall of the reservoir.

15. The assembly of claim 1, wherein the laser light is directed inside the reservoir at a height of between ½ inch to 1 inch above the base.

* * * * *